United States Patent [19]

Sawa et al.

[11] Patent Number: 4,640,283

[45] Date of Patent: Feb. 3, 1987

[54] METHOD OF CURING ATHLETE'S FOOT BY LASER BEAM IRRADIATION

[75] Inventors: Shigeki Sawa, Kanazawa; Hiroshi Ueda, Komatsu, both of Japan

[73] Assignee: Shibuya Kogyo Co. Ltd., Ishikawa, Japan

[21] Appl. No.: 603,543

[22] Filed: Apr. 25, 1984

[30] Foreign Application Priority Data

Dec. 19, 1983 [JP] Japan .............................. 58-239563

[51] Int. Cl.$^4$ ............................................ A61N 5/00
[52] U.S. Cl. ................................................. 128/395
[58] Field of Search .............................. 128/395–398, 128/303.1, 399

[56] References Cited

U.S. PATENT DOCUMENTS 3,538,919 11/1970 Meyer ................................ 128/398
4,144,888 3/1979 Malyshev et al. ............... 128/303.1

FOREIGN PATENT DOCUMENTS 603393 4/1978 U.S.S.R. .............................. 128/395

OTHER PUBLICATIONS

Minton et al., "Quantitation . . . Laser", Surgical Forum, 1966, pp. 21, 22.
Koslow et al., "Therapy . . . with Laser Radiation", Laser + Elecktro-Optik, No. 2, vol. 11, 1979, pp. 36–37.
Ohshiro, "Dermatologic Laser Treatment . . . ", Laser + Elektro-Optik, No. 3, vol. 9, 1977, pp. 34–35.

Primary Examiner—Lee S. Cohen
Attorney, Agent, or Firm—Alan H. MacPherson; Steven F. Caserza; Richard Franklin

[57] ABSTRACT

A method for curing athlete's foot includes a step of carrying out an irradiation of a laser beam having the energy density of 2 Joules/cm$^2$ for a time period of 10 milliseconds or less to the affected part of a patient's foot.

5 Claims, 3 Drawing Figures

Fig. 1
| TEMP. (°C) TIME (SEC.) | 50 | 60 | 70 | 90 |
|---|---|---|---|---|
| 1 | 14 | 25 | 67 | 100 |
| 5 | 30 | 43 | 90 | 100 |
| 10 | 60 | 87 | 92 | 100 |
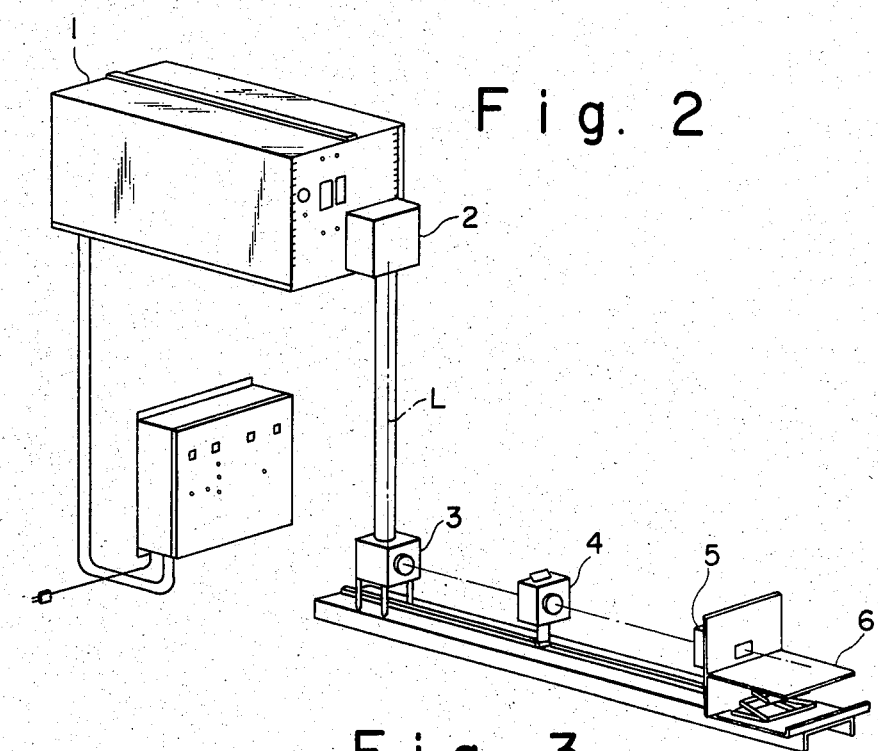
Fig. 2
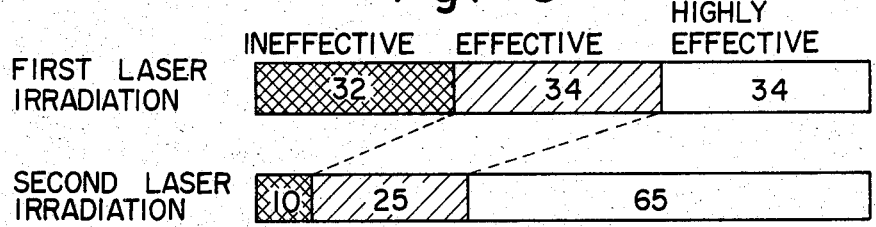
Fig. 3

METHOD OF CURING ATHLETE'S FOOT BY LASER BEAM IRRADIATION

BACKGROUND OF THE INVENTION

1. Field of the Invention

This invention relates to a treatment method of athlete's foot and particularly to a method for curing dermatophytosis or athlete's foot by application of heat thereto. More specifically, the present invention relates to a medical application of a laser beam for curing athlete's foot by killing ringworms by burning.

2. Description of the Prior Art

Various methods have been proposed to treat athlete's foot. The athlete's foot is dermatophytosis of the foot caused by ringworms living in the skin surface, and the currently most common treatment method is a chemical therapy, including application of a medical substance to the affected part and dosage of an antibiotic substance. The other methods include application of heat to the affected part by hot water or infrared lamp. However, none of these prior art methods is satisfactory and there has been a need to develop an improved method for curing athlete's foot.

Among the various treatment methods, attention here will be focused on the thermal treatment method in which heat is applied to the affected part of a foot. FIG. 1 is a table showing the measured results of lethality in % of ringworms with applied temperature and time taken as parameters. It is seen from the graph that the application of heat approximately at 90° C. or more for one second can kill the ringworms completely. However, to heat the affected part of a patient's foot to such a high temperature by hot water or infrared lamp is practically impossible because other side effects, such as burn, will be brought about.

Therefore, in accordance with the prior art thermal treatment method, it has been common practice to heat the affected part to 50° C. for about 10 seconds, which is considered to be a tolerable upper limit for a human being. Under the condition, the lethality of ringworms is 60% as shown in the table. If the time of heat application is reduced to 5 seconds, the lethality of ringworms drops to 30%. It is also seen from the table that the lethality of ringworms decreases as the temperature is decreased below 50° C. Thus, the conventional thermal treatment method has not been effective because, in order for it to be effective, a higher temperature must be maintained for a longer time duration, which then causes the patient to undergo an uncomfortable process. On the other hand, if the treatment conditions are set to be comfortable for the patient, then the effectiveness in treatment decreases dramatically and the lethality of ringworms becomes 50% or less, which is unsatisfactory in many respects.

In the meantime, medical applications of various lasers, such as $CO_2$ laser and YAG laser, in various fields of medical treatments and therapies are becoming increasingly popular. However, so far, no proposal has been made to use $CO_2$ laser and YAG laser for the treatment of athlete's foot. For example, the $CO_2$ laser has been mostly used as a laser surgical knife, and it has also been used to remove a trauma and a burn. In this case, however, the heat energy of a laser beam emitted from the $CO_2$ laser is used to have that portion of the tissue which is irradiated by the laser beam evaporated to carry out cutting of tumor tissue or removal of trauma or burn. In this technique, the laser beam is used at such an extremely high temperature as to cause evaporation of a laser-irradiated portion of the tissue, and, thus, this technique cannot be directly applied to the treatment of athlete's foot.

SUMMARY OF THE INVENTION

It is therefore a primary object of the present invention to provide an improved method for treating dermatophytosis Another object of the present invention is to provide an improved method for curing athlete's foot.

A further object of the present invention is to provide an improved thermal treatment method for curing athlete's foot.

A still further object of the present invention is to provide a method for curing athlete's foot by irradiation of a laser beam.

Other objects, advantages and novel features of the present invention will become apparent from the following detailed description of the invention when considered in conjunction with the accompanying drawings.

BRIEF DESCRIPTION OF THE DRAWINGS

FIG. 1 is a table showing the measured results of lethality in % of ringworms with temperature and time taken as parameters;

FIG. 2 is a perspective view showing the overall structure of a device for practicing the present invention; and FIG. 3 is a schematic illustration showing the experimental results of the present invention.

DESCRIPTION OF THE PREFERRED EMBODIMENTS

The present invention has been made on the basis of the recognition that ringworms only live in the epidermis or the surface layer of the skin, and more exactly in the stratum corneum or horney layer, which is the outermost layer of the epidermis and heat-sensitive nerves extend up to the corium or the true skin and they do not extend into the horney layer, and that if an irradiation of a laser beam having the energy density of a predetermined amount or more to the affected part of a foot is momentarily carried out for a predetermined time duration or less, the horney layer can be heated to a temperature which is suitable for the treatment of athlete's foot, e.g., 70° C. or more, while maintaining the temperature of the true skin, where the heat-sensitive nerves exist, so low as substantially not causing any burn to the true skin.

Stated more in detail, as long as an irradiation of laser beam is such that the laser beam has an appropriate magnitude of energy density and the irradiation of laser beam is momentary and limited to a predetermined time duration or less, even if the horney layer is heated to a temperature effective to kill the ringworms living therein, the heat thus produced in the horney layer is effectively dissipated through the skin so that the temperature substantially drops to a low level by the time in which the heat reaches the heat-sensitive nerves in the true skin thereby preventing the patient from feeling heat. Accordingly, in order to relieve the patient from feeling hotness during treatment, it is necessary that heating due to irradiation of a laser beam take place only at the surface of the epidermis, or more preferably within the horney layer, and not in the true skin. With such heating, an excellent treatment of athlete's foot can be carried out without causing the patient to feel heat.

Under the circumstances, in accordance with the present invention, the conditions of a laser beam which can be advantageously used for the treatment of athlete's foot without requiring a significant endurance against heat to the patient are set such that the laser beam has the energy density of 2 Joules/cm$^2$ or more and the time period of a single laser beam irradiation is 10 milliseconds or less. The condition for obtaining the energy density of 2 Joules/cm$^2$ by a laser beam irradiation for a time period of 10 milliseconds is considered to be substantially an upper limit in which the patient can tolerate heat and an excellent treatment of athlete's foot can be carried out by a single laser beam shot. In other words, the duration of the shot is increased beyond 10 milliseconds, it will become possible for the patient to tolerate heat by making the energy density less than 2 Joules/cm$^2$. However, this will then cause the cure rate of athlete's foot to decrease. It is thus considered that in the case where the irradiation time period is set beyond 10 milliseconds, even if the energy density of an approximately upper tolerable limit against heat, which is 2 Joules/cm$^2$ or less, is given, the temperature of the true skin increases significantly though the horney layer is not sufficiently heated to a temperature suitable for the treatment of athlete's foot.

On the other hand, in the case where the pulse duration is set shorter, the energy density can be increased more than 2 Joules/cm$^2$ up to a point where air breakdown due to the high electric field takes place at the surface of the skin. As the pulse duration becomes shorter, the problem of heat practically disappears. In such a case, however, since it is difficult to heat the horney layer to a temperature level suitable for the treatment of athlete's foot by a single shot, it is necessary to use a multiple laser shot. In such a case, the patient will come to sense heat as the number of irradiations increases. However, as long as the treatment conditions are set within the above-described energy density and pulse durations, the feeling of tolerable heat by the patient indicates that the horney layer is heated to a temperature at which the athlete's foot can be cured in an excellent manner.

In the present invention, it is preferable to use a laser, such as a CO$_2$ laser or a YAG laser, which emits a laser beam of the infrared region, having a wavelength of 0.7 micrometers or more, and which is excellent in thermal effect. It is also preferable not to use a laser, such as a N$_2$ laser and an excimer laser, which emits a laser beam of the ultraviolet region because of the possible inducement of cutaneous cancer.

In general, the thickness of the horney layer differs depending on the parts of a body, such as the sole of a foot and the neck; however, it generally ranges between 50 and 2,000 micrometers. On the other hand, the light dispersion length or penetration length of a laser beam from a CO$_2$ gas laser into the skin is approximately 50 micrometers and that of a YAG laser is approximately 800 micrometers. It is thus preferable to use the CO$_2$ laser for treatment of thinner portions of the epidermis. For thicker portions of the epidermis, the outer side of the horney layer is heated by irradiation of a laser beam and the inner portion of the horney layer must be heated by conduction of heat. Such heating due to heat conduction indicates that heat is also transferred to the heat-sensitive nerves in the true skin, which tends to limit the application of a CO$_2$ laser for thicker portions of the epidermis.

On the other hand, a YAG laser beam has a relatively long penetration length and thus there is a possibility that the laser beam directly reaches the true skin at a location where the epidermis is relatively thin, which indicates difficulty in the application of a YAG laser where the epidermis is thin. However, the YAG laser has an advantage to use it at a location where the epidermis is thick because all over the horney layer can be heated directly by a YAG laser beam; on the contrary, the heating by CO$_2$ laser beam must rely on thermal conduction. It is thus most preferable to use the CO$_2$ laser and the YAG laser selectively or another laser capable of emitting a laser beam having an optimum penetration length in consideration of the thickness of the epidermis and horney layer at a location where treatment is to be carried out.

Between the CO$_2$ and YAG lasers, since the penetration length is longer for the YAG laser, the patient tends to feel more heat when irradiated by a YAG laser beam. However, at a location where the skin is relatively thick, the energy density and pulse duration of a laser beam which can be advantageously used to treat the athlete's foot without requiring the patient to significantly endure against heat have been found to range within the before-mentioned conditions both for the CO$_2$ and YAG lasers.

FIG. 2 is a perspective view showing the overall structure of a device for treating the athlete's foot constructed for the present invention employing a high power, pulsed TEA CO$_2$ laser 1. A top reflecting mirror 2 is mounted in front of the laser 1 to direct a laser beam emitted from the laser 1 vertically downward to a bottom reflecting mirror 3 which directs a laser beam L in the horizontal direction. After reflection, the laser beam L passes through an aperture 4 where the amount of laser energy is varied. Then, the laser beam passing through the aperture 4 passes through a focusing lens 5 to be focused at a predetermined position in front of a foot rest 6 on which the patient can place his or her foot to be irradiated by the laser beam. As shown, the foot rest 6 includes a vertical wall whose surface is perpendicular to the optical path of the laser beam L, and the vertical wall is provided with a window through which the laser beam L passes and becomes focused at the predetermined position. Thus, the patient is only required to place his or her ailing foot as pressed against the vertical wall. Although not illustrated specifically, there is preferably disposed an evacuating device in the vicinity of the foot rest 6 so as to have the smoke produced when the foot is irradiated by the laser beam evacuated. Furthermore, also preferably disposed is a trigger switch in the vicinity of the foot rest 6 for triggering the operation of the laser 1 to emit the required laser beam L.

In operation, when the trigger switch (not shown) is turned on, the laser 1 emits the laser beam L, which is reflected by the mirrors 2 and 3 and whose output energy level is adjusted by the aperture device 4, and the thus regulated laser beam L passes through the focusing lens 5 to be focused on the affected part of the patient foot placed on the foot rest 6 against its vertical wall with the window.

Using the setup shown in FIG. 2, experiments were carried out. The pulsed TEA CO$_2$ laser 1 used had the parameters: output wave length of 10.6 micrometers, pulse duration of 1 micro-second, and output energy of 2.5 Joules/pulse. In one experiment, the output energy of 2.5 Joules/pulse was focused on an area of approximately 7 mm×7 mm, which corresponds to the irradiation energy density of 5.1 Joules/cm$^2$. In another experiment, the above-mentioned output energy was lowered by the aperture device 4 and focused on an area of approximately 2 mm×2 mm, which corresponds to the irradiation energy density of 10-20 Joules/cm$^2$. In a further experiment, the above-mentioned output energy was lowered by the aperture device 4 and focused on an area of approximately 1 mm×1 mm, which corresponds to the irradiation energy density of approximately 30 Joules/cm$^2$. In all of these cases, there were obtained virtually the same results.

In the above-described experiments, since the pulse duration was a relatively short time period of 1 microsecond, almost no heat was felt by one single laser shot in either one of the above-mentioned three different energy densities and thus the laser beam irradiation could be carried out 3-4 times repetitively at a small interval and the repetition limit ranged 4-5 times. Under the circumstances, with a single laser beam irradiation, the surface of the irradiated skin burnt and carbonized to white and the color gradually changed to dark brown as the number of shots was increased. Although endurance against heat differed from one patient to another, the most sensitive patient felt only a light smarting.

The treatment in this case was done one session per week for two weeks and for each treatment examination by culture was carried out. In this examination, since the conditions of the affected parts differed not only from one patient to another but also from one location to another of the same patient, the affected part was divided into a plurality of examination regions, each having the area of approximately 2×3 cm$^2$, and the thickness of the horney layer was regarded as being uniform throughout the examination region. Then, from each of the examination regions, eight skin pieces, each having the size of 2 mm×2 mm, were collected as samples, which were then subjected to culture examination to measure the lethality of ringworms for each of the samples. In collecting samples, that portion of the skin having the standard thickness of 0.3-0.6 mm was selected.

FIG. 3 indicates the results of the culture examination for the eight samples collected from each of the examination regions. In FIG. 3, "INEFFECTIVE" indicates the cure rate of eight samples to be 19% or less and "EFFECTIVE" and "HIGHLY EFFECTIVE" indicate the cure rate to be 20-69% and 70% or more, respectively. As can be understood from the results shown in FIG. 3, with the first laser beam irradiation, the results were distributed substantially equally among "INEFFECTIVE", "EFFECTIVE" and "HIGHLY EFFECTIVE", thereby indicating the net cure rate of approximately ⅔. Then, with the second laser beam irradiation which was carried out one week later, the net cure rate increased to about 90% with the % ratio of "HIGHLY EFFECTIVE" being nearly 70%. Of importance, as described previously, the patient can select the number of repetitive irradiations by himself within the above-mentioned range of 3-5 in each every other week session, and, thus, it is not necessary for the patient to tolerate heat more than necessary and still an excellent treatment of athlete's foot can be carried out.

In the above-described experiment, the laser beam irradiation was carried out using a laser beam having the energy density of 2 Joules/cm$^2$ for a duration of 10 milliseconds or less. In the other experiments within the above-mentioned conditions, similar results were obtained as far as the cure rate was concerned though there were slight differences in the feeling of heat.

While the above provides a full and complete disclosure of the preferred embodiments of the present invention, various modifications, alternate constructions and equivalents may be employed without departing from the true spirit and scope of the invention. Therefore, the above description and illustration should not be construed as limiting the scope of the invention, which is defined by the appended claims.

What is claimed is:

1. A method for curing athlete's foot by applying a laser beam having the energy density of 2 Joules/cm$^2$ or more to an area of a person's skin affected by dermatophytosis for a predetermined time period of 10 milliseconds or less at least once.

2. The method of claim 1 wherein said laser beam has a wavelength of 0.7 micrometers or more.

3. The method of claim 2 wherein said laser beam is emitted from a $CO_2$ gas laser.

4. The method of claim 2 wherein said laser beam is emitted from a YAG laser.

5. A method for curing dermatophytosis by applying a laser beam having a selected energy density to the area of skin affected by dermatophytosis for a predetermined time, said energy density and predetermined time being selected so that irradiation of the skin takes place only at the surface of the epidermis in the horney layer and the horney layer is heated to 70° C. or more while maintaining the temperature of the true skin beneath the horney layer where heat-sensitive nerves exist so low as substantially not to burn the true skin.

* * * * *